United States Patent
Muhr et al.

(10) Patent No.: US 10,767,160 B2
(45) Date of Patent: Sep. 8, 2020

(54) METHODS FOR MODULATING PRODUCTION PROFILES OF RECOMBINANT PROTEINS

(71) Applicant: ARES TRADING S.A., Aubonne (CH)

(72) Inventors: Anais Muhr, Champigneulles (FR); David Bruhlmann, Lausanne (CH); Martin Jordan, Ecublens (CH); Herve Broly, Chatel-St-Denis (CH); Matthieu Stettler, Sierre (CH)

(73) Assignee: ARES TRADING S.A., Aubonne (CH)

( * ) Notice: Subject to any disclaimer, the term of this patent is extended or adjusted under 35 U.S.C. 154(b) by 59 days.

(21) Appl. No.: 15/743,714

(22) PCT Filed: Jul. 7, 2016

(86) PCT No.: PCT/EP2016/066147
§ 371 (c)(1),
(2) Date: Jan. 11, 2018

(87) PCT Pub. No.: WO2017/012886
PCT Pub. Date: Jan. 26, 2017

(65) Prior Publication Data
US 2018/0201897 A1    Jul. 19, 2018

(30) Foreign Application Priority Data
Jul. 17, 2015 (EP) .................................... 15177224

(51) Int. Cl.
C12N 5/00 (2006.01)
C12N 15/67 (2006.01)
C07K 16/18 (2006.01)
C07K 16/28 (2006.01)

(52) U.S. Cl.
CPC ............ *C12N 5/0018* (2013.01); *C07K 16/18* (2013.01); *C07K 16/28* (2013.01); *C12N 15/67* (2013.01); *C07K 2317/21* (2013.01); *C07K 2317/24* (2013.01); *C12N 2501/999* (2013.01); *C12N 2511/00* (2013.01)

(58) Field of Classification Search
None
See application file for complete search history.

(56) References Cited

U.S. PATENT DOCUMENTS

| | | | |
|---|---|---|---|
| 2007/0077552 A1* | 4/2007 | Hecht | G01N 33/6896 435/4 |
| 2018/0201896 A1 | 7/2018 | Muhr et al. | |
| 2018/0312802 A1 | 11/2018 | Bielser et al. | |
| 2018/0320128 A1 | 11/2018 | Bruhlmann et al. | |

FOREIGN PATENT DOCUMENTS

| WO | WO 01/59069 | 8/2001 |
|---|---|---|
| WO | WO 2008/068879 | 6/2008 |
| WO | WO 2010/102114 | 9/2010 |
| WO | WO 2014/110440 | 7/2014 |
| WO | WO 2014/151901 | 9/2014 |
| WO | WO 2017/012883 | 1/2017 |

OTHER PUBLICATIONS

Sugai M et al. A triazine dye, cibacron blue 3G-A induces *Staphylococcus aureus* to form giant clusters. 1990. FEMS Microbiology Letters 67:175-178. (Year: 1990).*
Wurm FM. Production of Recombinant Protein Therapeutics in Cultivated Mammalian Cells. 2004. Nature Biotechnology. vol. 22, No. 11. p. 1393-1398 (Year: 2004).*
Hossler, P. et al. "Improvement of Mammalian Cell Culture Performance Through Surfactant Enabled Concentrated Feed Media" *Biotechnology Progress*, May 11, 2013, pp. 1023-1033, vol. 29, No. 4.
Kim, N. S. et al. "Overexpression of bcl-2 Inhibits Sodium Butyrate-Induced Apoptosis in Chinese Hamster Ovary Cells Resulting in Enhanced Humanized Antibody Production" *Biotechnology and Bioengineering*, Jan. 1, 2000, pp. 184-193, vol. 71, No. 3.
Miller, K. J. et al. "Cibacron blue allosterically modulates the rat $P2X_4$ receptor" *Neuropharmacology*, Dec. 1, 1998, pp. 1579-1586, vol. 37, No. 12.
Written Opinion in International Application No. PCT/EP2016/066147, dated Sep. 14, 2016, pp. 1-6.
Currently Pending Claims of U.S. Appl. No. 15/772,819, dated May 2, 2018.
Currently Pending Claims of U.S. Appl. No. 15/773,186, dated May 3, 2018.

* cited by examiner

*Primary Examiner* — Paul J Holland
(74) *Attorney, Agent, or Firm* — Saliwanchik, Lloyd & Eisenschenk

(57) ABSTRACT

The invention is in the field of cell culture. Particularly the invention relates to methods of culturing a host cell expressing a recombinant protein in a cell culture medium comprising an effective amount of a triazine dye or supplemented with an effective amount of a triazine dye, whereby production of said protein is increased relative to cells grown without said triazine dye or any other inducer.

3 Claims, 12 Drawing Sheets

Figure 1 (con't)

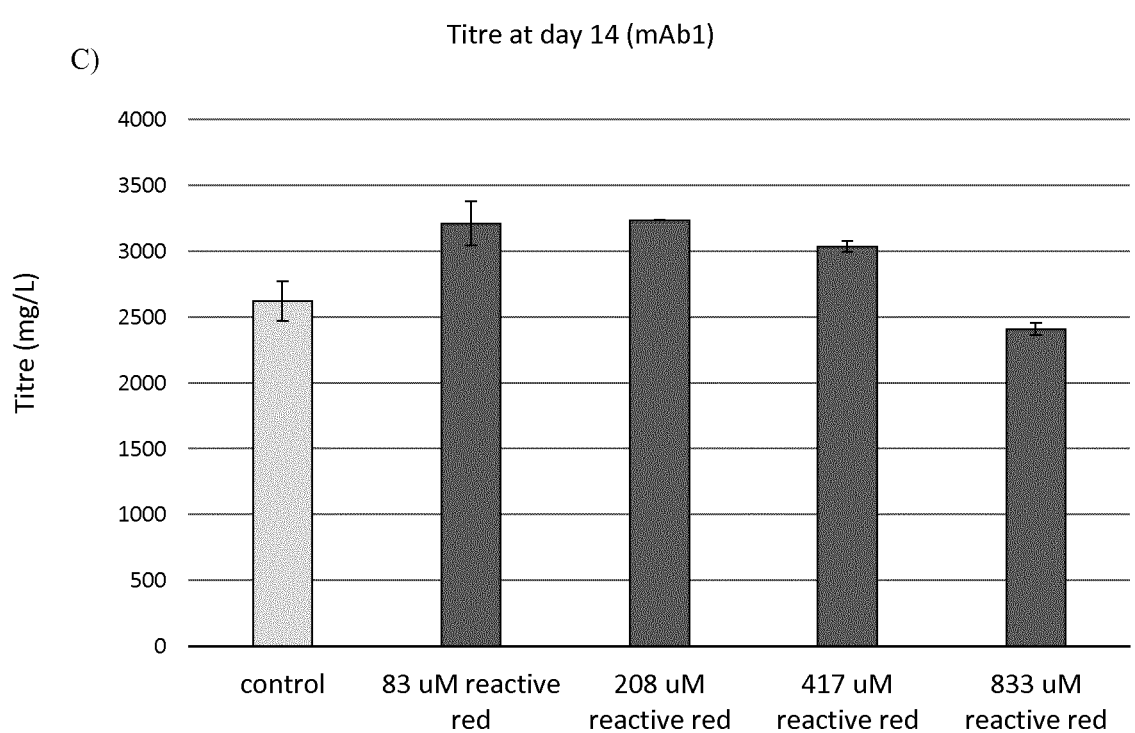
Figure 3 (Con't)

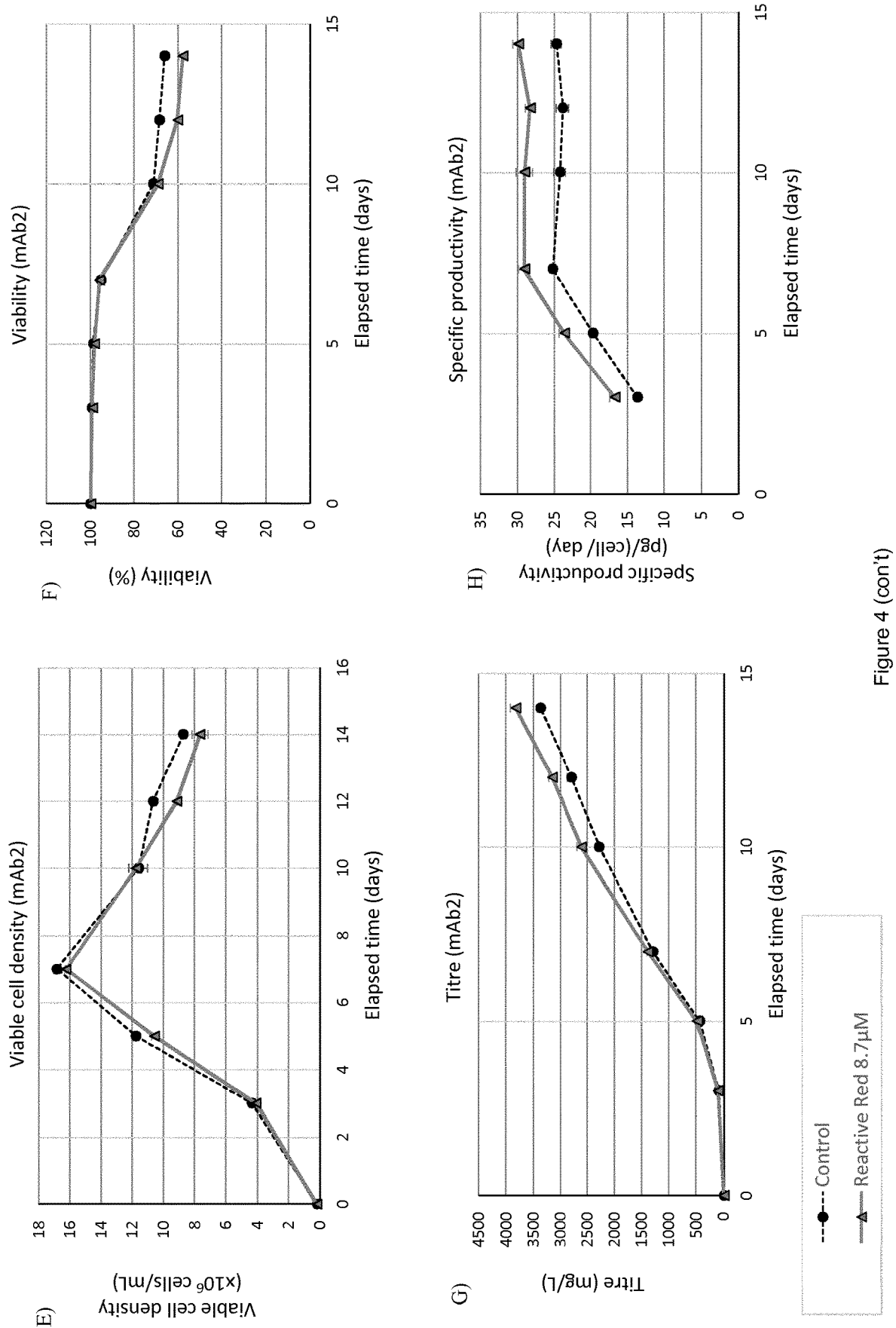
Figure 4 (con't)

A)

B)

Figure 6 (con't)

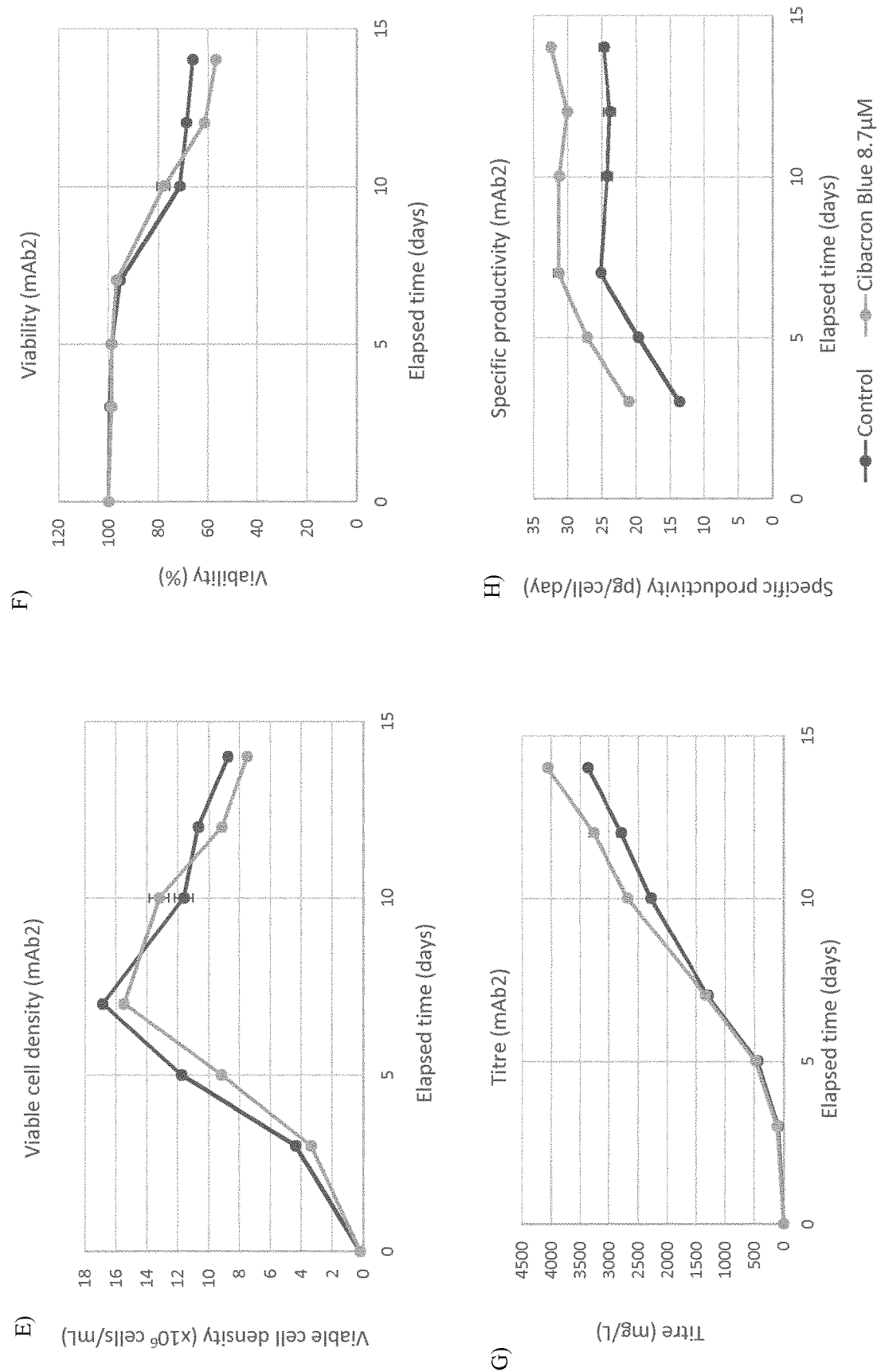
Figure 8 (Con't)

METHODS FOR MODULATING PRODUCTION PROFILES OF RECOMBINANT PROTEINS

CROSS-REFERENCE TO RELATED APPLICATION

This application is the U.S. national stage application of International Patent Application No. PCT/EP2016/066147, filed Jul. 7, 2016.

FIELD OF THE INVENTION

The invention is in the field of cell culture. Particularly the invention relates to methods of culturing a host cell expressing a recombinant protein in a cell culture medium comprising an effective amount of a triazine dye or supplemented with an effective amount of a triazine dye, whereby production of said protein is increased relative to cells grown without said triazine dye or any other inducer.

BACKGROUND OF THE INVENTION

Optimisation of culture conditions to obtain the greatest possible productivity is one of the main aim of recombinant protein production. Even marginal increases in productivity can be significant from an economical point of view. Many commercially relevant proteins are produced recombinantly in host cells. This leads to a need to produce these proteins in an efficient and cost effective manner. Unfortunately, one of the drawback of recombinant protein production is that the conditions in which cell culture is performed usually favors a reduction of cell viability over time, reducing both efficiency and overall productivity.

Perfusion culture, Batch culture and Fed batch culture are the basic methods for culturing animal cells for producing recombinant proteins.

Very often, especially in fed-batch and perfusion methods, inducing agents are added to the culture media to increase production of proteins in cells. These inducers induce the cell to produce more desired product. One such agent is sodium butyrate. However, the drawback of using sodium butyrate in cell culture is that it affects significantly cell viability. For instance Kim et al (2004) have shown that although sodium butyrate was able to increase protein production in recombinant CHO cells in a batch culture, at the end of the production run (after 8 days of culture), cell viability was less than 45%. Repeating the same experiments in perfusion batch culture, the authors noticed that within 6 days of treatment, cell viability was as low as 15%.

Although the use of an inducer can increase protein production, the drawback concerning cell viability has to be considered. Indeed, the use of a well-known inducer, such as sodium butyrate, can be counterproductive after about 5 days in culture, whereas a typical production period is between 12 to 15 days in fed-batch mode and can be up to 40-45 days in perfusion mode.

Because many proteins are recombinantly produced by cells grown in culture for more than 6 days, there is a need for methods allowing increased cell productivity and more efficient production runs, while maintaining acceptable cell viability over a longer time.

Therefore, there remains a need for culture conditions and production methods allowing for increased recombinant protein productivity by maintaining viable cell density, increasing the titre and/or avoiding substantial decrease in cell viability over a production period. The present invention addresses this need by providing methods and compositions for increasing production of recombinant proteins.

SUMMARY OF THE INVENTION

In one aspect the invention provides a method of increasing production of a recombinant protein, said method comprising culturing a host cell expressing said protein in cell culture medium comprising an effective amount of a triazine dye or supplemented with an effective amount of a triazine dye.

In a further aspect, the invention provides a method of increasing production of a recombinant protein, said method comprising culturing a host cell expressing said protein in cell culture medium complemented with at least one feed comprising an effective amount of a triazine dye.

In another aspect, the invention provides a method of culturing a host cell that expresses a recombinant protein, said method comprising culturing said host cell in cell culture medium comprising an effective amount of a triazine dye or supplemented with an effective amount of a triazine dye.

In another aspect, the invention provides a composition comprising a cell culture medium comprising an effective amount of a triazine dye or supplemented with an effective amount of a triazine dye.

In a further aspect, the invention provides use of a triazine dye in a cell culture medium for increasing production of recombinant proteins.

Gal=Galactosylation; Man=Mannosylation; Fuc=Fucosylation; Sial=sialylation; Ukn=unknown.

Figure 6:
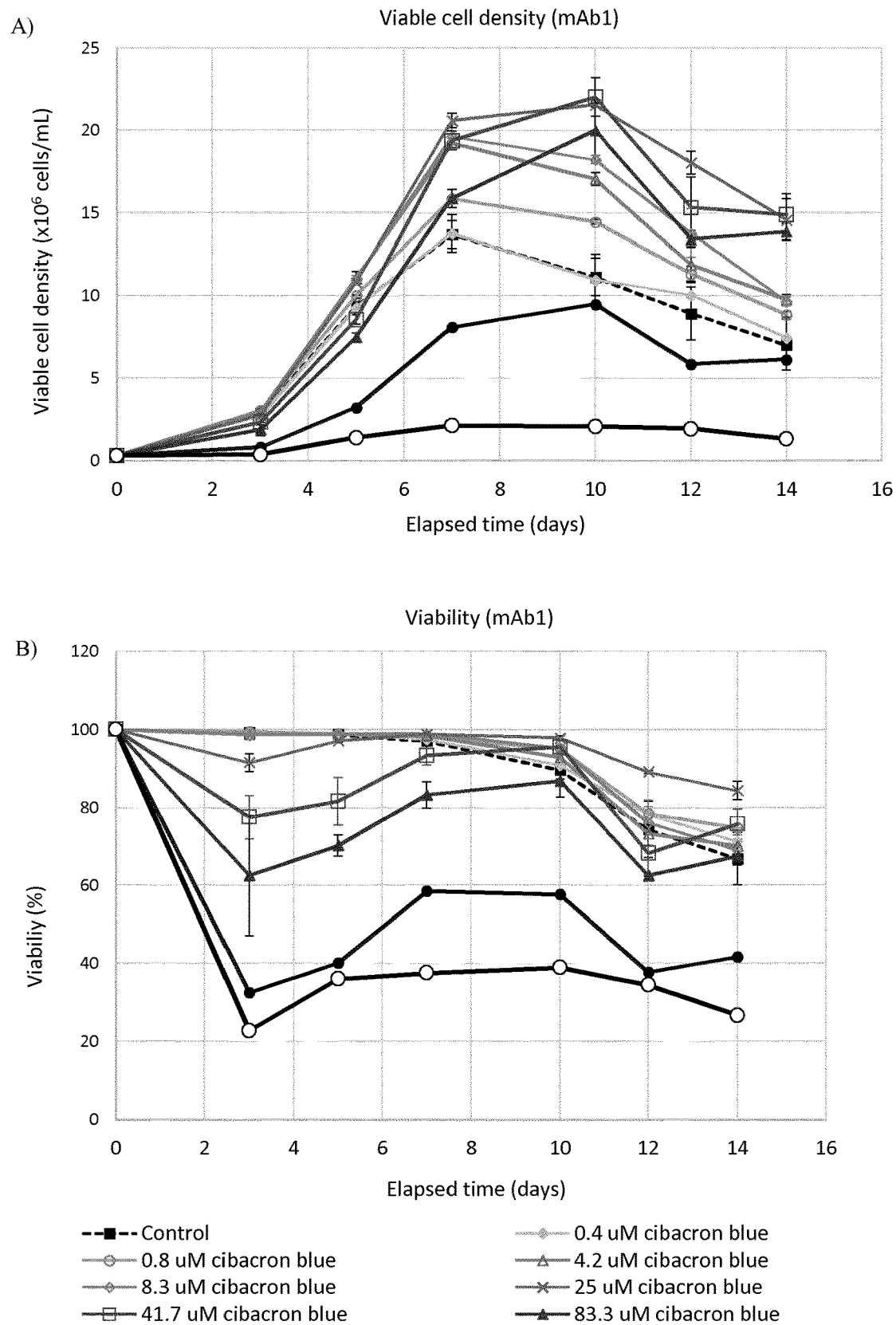

FIG. 6 shows the viable cell density (Guava®, FIG. 6A) and the viability (Guava®, FIG. 6B) in relation to time (until day 14), as well as the titre (Octet®, FIG. 6C) for the host cells expressing the antibody mAb1 cultured at different concentrations of Cibacron Blue 3GA in microplates. The results are shown as average value±standard deviation. Same legend for FIGS. 6A and 6B.

Figure 7:
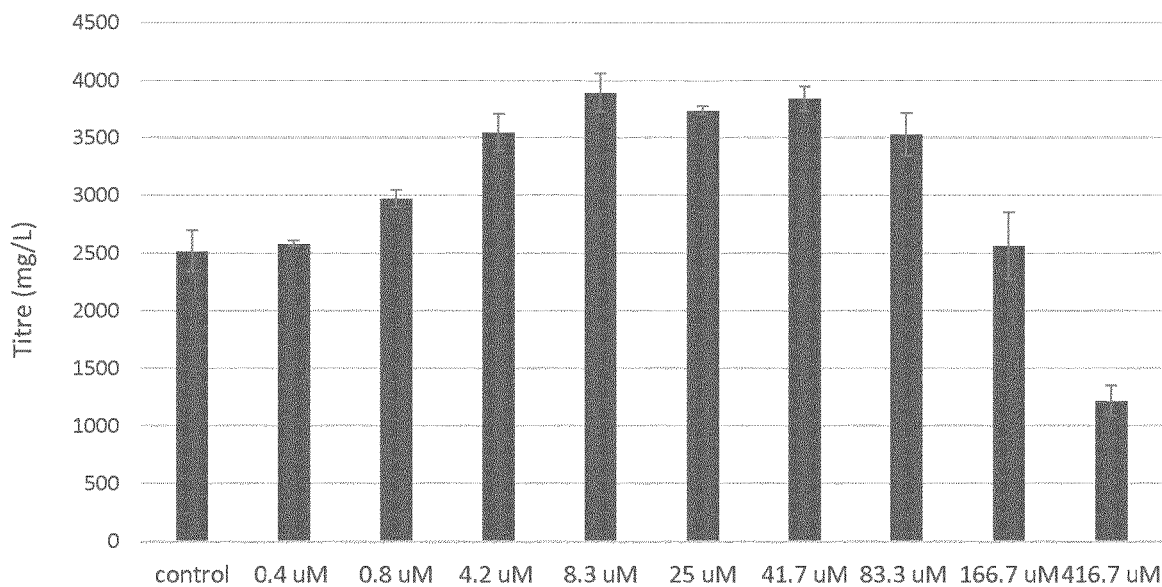
Figure 7:
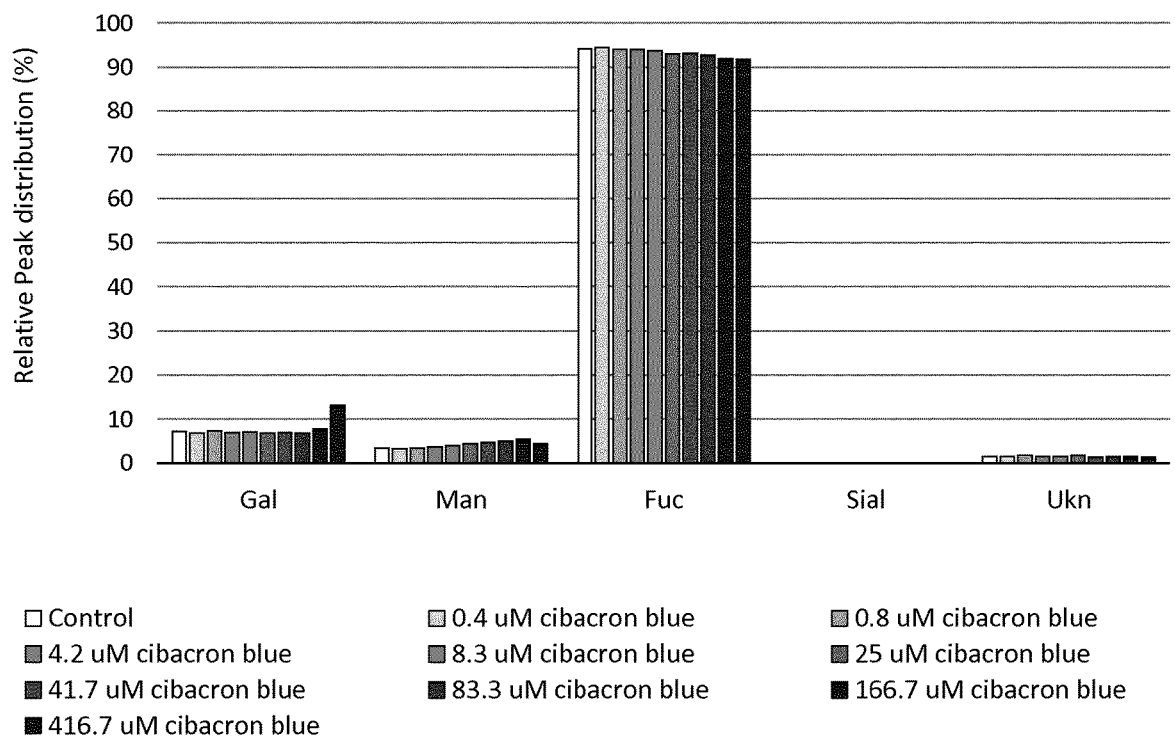

FIG. 7 shows quality analysis of the secreted antibody mAb1 at different concentrations of Cibacron Blue 3GA in microplate. Glycosylation profiles are analysed by CGE-LIF assay.

Figure 8:
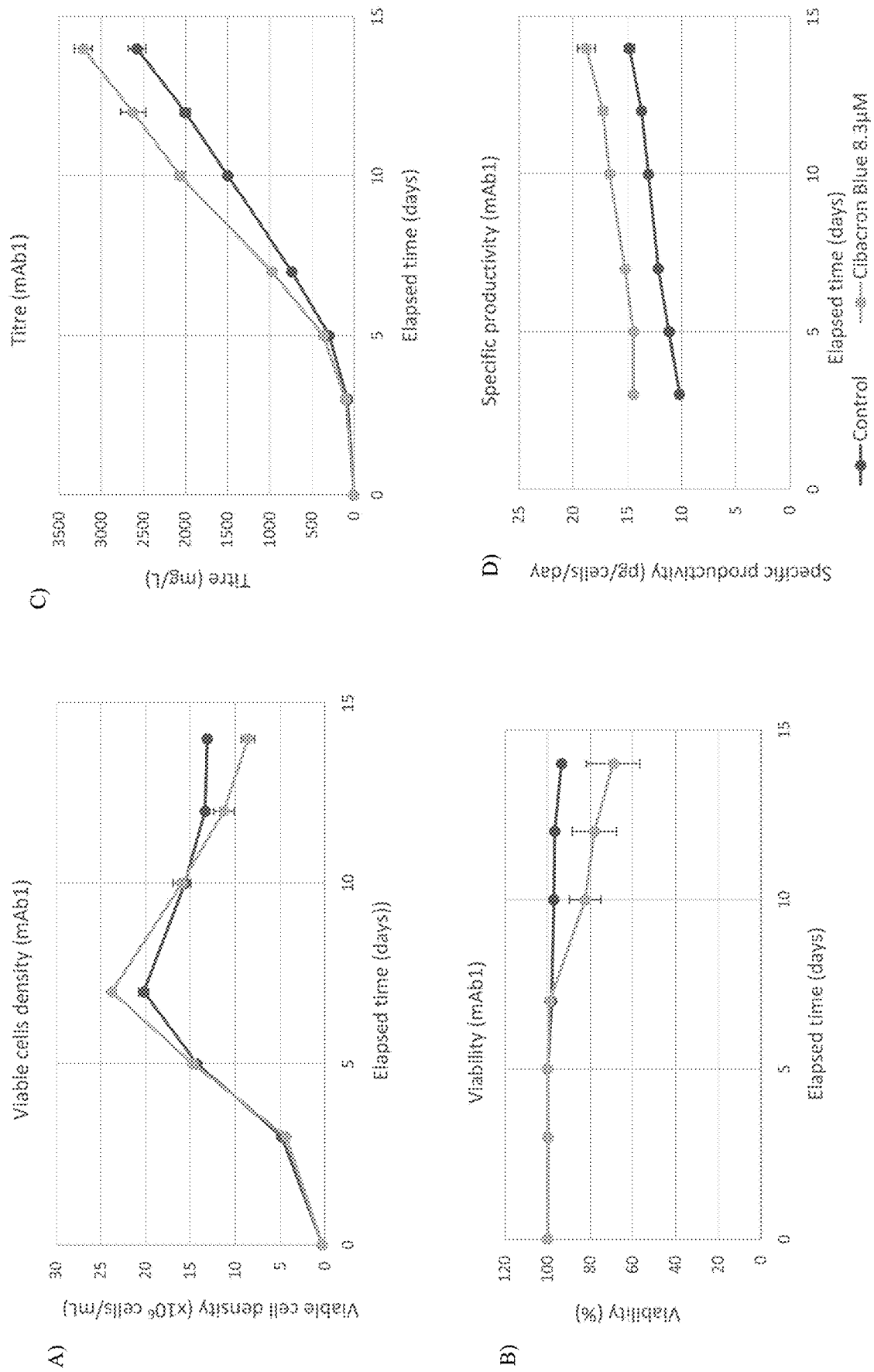

FIG. 8 shows the viable cell density (ViCell®, FIGS. 8A and 8E), the viability (ViCell®, FIGS. 8B and 8F), the titre (Biacore®, FIGS. 8C and 8G), the specific productivity (FIGS. 8D and 8H) in relation to time (until day 14) for the host cells expressing the antibody mAb1 (left) and the antibody mAb2 (right) cultured with different concentrations of Cibacron blue 3GA in Spin Tubes (average value±standard deviation). One legend for FIGS. 8A to 8D and one for FIGS. 8E to 8H.

Figure 9:
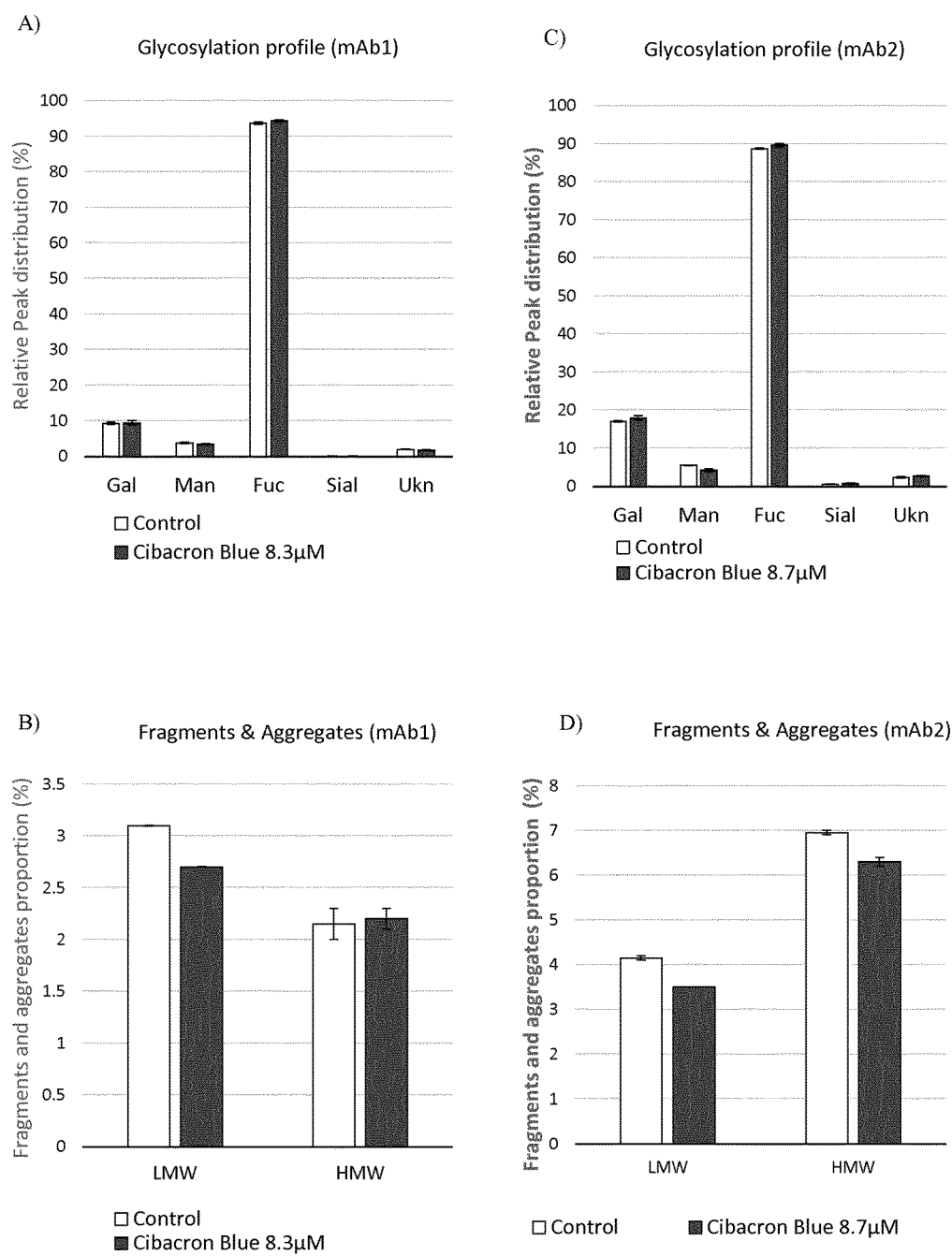

FIG. 9 shows glycosylation profile (CGE-LIF, FIGS. 9A and 9C) as well as aggregates and fragments ratios (SE HPLC and SDS-capillary gel electrophoresis, FIGS. 9B and 9D) for the antibodies mAb1 and mAb2 when the host cells are cultured at different concentrations of Cibacron Blue 3GA in Spin Tubes. The results are presented as average value±standard deviation. Gal=Galactosylation; Man=Mannosylation; Fuc=Fucosylation; Sial=sialylation; Ukn=unknown.

In the FIGS. 1-9: uM and µM both mean micromolar.

DETAILED DESCRIPTION OF THE INVENTION

All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control.

Unless defined otherwise, all technical and scientific terms used herein have the same meaning as is commonly understood by one of skill in art to which the subject matter herein belongs. As used herein, the following definitions are supplied in order to facilitate the understanding of the present invention.

As used in the specification and claims, the term "and/or" used in a phrase such as "A and/or B" herein is intended to include "A and B", "A or B", "A", and "B".

As used in the specification and claims, the term "cell culture" or "culture" is meant the growth and propagation of cells in vitro, i.e. outside of an organism or tissue. Suitable culture conditions for mammalian cells are known in the art, such as taught in Cell Culture Technology for Pharmaceutical and Cell-Based Therapies (2005). Mammalian cells may be cultured in suspension or while attached to a solid substrate.

The terms "cell culture medium," "culture medium", "medium," and any plural thereof, refer to any medium in which cells of any type can be cultured. A "basal medium" refers to a cell culture medium that contains all of the essential ingredients useful for cell metabolism. This includes for instance amino acids, lipids, carbon source, vitamins and mineral salts. DMEM (Dulbeccos' Modified Eagles Medium), RPMI (Roswell Park Memorial Institute Medium) or medium F12 (Ham's F12 medium) are examples of commercially available basal media. Alternatively, said basal medium can be a proprietary medium fully developed in-house, also herein called "chemically defined medium" or "chemically defined culture medium", in which all of the components can be described in terms of the chemical formulas and are present in known concentrations. The culture medium can be free of proteins and/or free of serum, and can be supplemented by any additional compound(s) such as amino acids, salts, sugars, vitamins, hormones, growth factors, depending on the needs of the cells in culture.

The term "feed medium" (and plural thereof) refers to a medium used as a supplementation during culture to replenish the nutrients which are consumed. The feed medium can be a commercially available feed medium or a proprietary feed medium (herein alternatively chemically defined feed medium).

The term "bioreactor" or "culture system" refers to any system in which cells can be cultured, preferably in batch or fed-batch mode. This term includes but is not limited to flasks, static flasks, spinner flasks, tubes, shake tubes, shake bottles, wave bags, bioreactors, fibre bioreactors, fluidised bed bioreactors, and stirred-tank bioreactors with or without microcarriers. Alternatively, the term "culture system" also includes microtitre plates, capillaries or multi-well plates. Any size of bioreactor can be used, for instance from 0.1 millilitre (0.1 mL, very small scale) to 20000 litres (20000 L or 20 KL, large scale), such as 0.1 mL, 0.5 mL 1 mL, 5 mL, 0.01 L, 0.1 L, 1 L, 2 L, 5 L, 10 L, 50 L, 100 L, 500 L, 1000 L (or 1 KL), 2000 L (or 2 KL), 5000 L (or 5 KL), 10000 L (or 10 KL), 15000 L (or 15 KL) or 20000 L (20 KL).

The term "fed-batch culture" refers to a method of growing cells, where there is a bolus or continuous feed media supplementation to replenish the nutrients which are consumed. This cell culture technique has the potential to obtain high cell densities in the order of greater than $10 \times 10^6$ to $30 \times 10^6$ cells/ml, depending on the media formulation, cell line, and other cell growth conditions. A biphasic culture condition can be created and sustained by a variety of feed strategies and media formulations.

Alternatively a perfusion culture can be used. Perfusion culture is one in which the cell culture receives fresh perfusion feed medium while simultaneously removing spent medium. Perfusion can be continuous, step-wise, intermittent, or a combination of any or all of any of these. Perfusion rates can be less than a working volume to many working volumes per day. Preferably the cells are retained in the culture and the spent medium that is removed is substantially free of cells or has significantly fewer cells than the culture. Perfusion can be accomplished by a number of cell retention techniques including centrifugation, sedimentation, or filtration (see for example Voisard et al., 2003). When using the methods and/or cell culture techniques of the instant invention, the recombinant protein are generally directly secreted into the culture medium. Once said protein is secreted into the medium, supernatants from such expression systems can be first concentrated using a commercially available protein concentration filter.

As used herein, "cell density" refers to the number of cells in a given volume of culture medium. "Viable cell density" refers to the number of live cells in a given volume of culture medium, as determined by standard viability assays. The terms "Higher cell density" or "Higher viable cell density", and equivalents thereof, means that the cell density or viable cell density is increased by at least 15% compared to the control culture condition. The cell density will be considered as maintained if it is in the range of −15% to 15% compared to the control culture condition. The terms "Lower cell density" or "Lower viable cell density", and equivalents thereof, means that the cell density or viable cell density is decreased by at least 15% when compared to the control culture condition.

The term "viability", or "cell viability" refers to the ratio between the total number of viable cells and the total number of cells in culture. Viability is usually acceptable as long as it is at not less than 60% compared to the start of the culture (however, the acceptable threshold can be determined case by case). Viability is often used to determine time for harvest. For instance, in fed-batch culture, harvest can be performed once viability falls at 60% or after 14 days in culture.

The wording "titre" refers to the amount or concentration of a substance, here the protein of interest, in solution. It is an indication of the number of times the solution can be diluted and still contain detectable amounts of the molecule of interest. It is calculated routinely for instance by diluting serially (1:2, 1:4, 1:8, 1:16, etc.) the sample containing the protein of interest and then using appropriate detection method (colorimetric, chromatographic etc.), each dilution is assayed for the presence of detectable levels of the protein of interest. Titre can also be measured by means such as by fortéBIO Octet® or with Biacore C®, as per the example section.

The term "specific productivity" refers to the amount of a substance, here the protein of interest, produced per cell per day.

The terms "higher titre" or "higher specific productivity", and equivalents thereof, means that the titre or the productivity is increased by at least 10% when compared to the control culture condition. The titre or specific productivity will be considered as maintained if it is in the range of −10% to 10% compared to the control culture condition. The terms "lower titre" or "lower productivity", and equivalents thereof, means that the titre or the productivity is decreased by at least 10% when compared to the control culture condition.

The term "protein" as used herein includes peptides and polypeptides and refers to compound comprising two or more amino acid residues. A protein according to the present invention includes but is not limited to a cytokine, a growth factor, a hormone, a fusion protein, an antibody or a fragment thereof. A therapeutic protein refers to a protein that can be used or that is used in therapy.

The term "recombinant protein" means a protein produced by recombinant technics. Recombinant technics are well within the knowledge of the skilled person (see for instance Sambrook et al., 1989, and updates).

As used in the specification and claims, the term "antibody", and its plural form "antibodies", includes, inter alia, polyclonal antibodies, affinity-purified polyclonal antibodies, monoclonal antibodies, and antigen-binding fragments, such as F(ab')2, Fab proteolytic fragments, and single chain variable region fragments (scFvs). Genetically engineered intact antibodies or fragments, such as chimeric antibodies, scFv and Fab fragments, as well as synthetic antigen-binding peptides and polypeptides, are also included.

The term "humanised" immunoglobulin refers to an immunoglobulin comprising a human framework region and one or more CDRs from a non-human (usually a mouse or rat) immunoglobulin. The nonhuman immunoglobulin providing the CDRs is called the "donor" and the human immunoglobulin providing the framework is called the "acceptor" (humanisation by grafting non-human CDRs onto human framework and constant regions, or by incorporating the entire non-human variable domains onto human constant regions (chimerisation)). Constant regions need not be present, but if they are, they must be substantially identical to human immunoglobulin constant regions, i.e., at least about 85-90%, preferably about 95% or more identical. Hence, all parts of a humanised immunoglobulin, except possibly the CDRs and a few residues in the heavy chain constant region if modulation of the effector functions is needed, are substantially identical to corresponding parts of natural human immunoglobulin sequences. Through humanising antibodies, biological half-life may be increased, and the potential for adverse immune reactions upon administration to humans is reduced.

As used in the specification and claims, the term "fully human" immunoglobulin refers to an immunoglobulin comprising both a human framework region and human CDRs. Constant regions need not be present, but if they are, they must be substantially identical to human immunoglobulin constant regions, i.e., at least about 85-90%, preferably about 95% or more identical. Hence, all parts of a fully human immunoglobulin, except possibly few residues in the heavy chain constant region if modulation of the effector functions or pharmacokinetic properties are needed, are substantially identical to corresponding parts of natural human immunoglobulin sequences. In some instances, amino acid mutations may be introduced within the CDRs, the framework regions or the constant region, in order to improve the binding affinity and/or to reduce the immunogenicity and/or to improve the biochemical/biophysical properties of the antibody.

The term "recombinant antibodies" means antibodies produced by recombinant technics. Because of the relevance of recombinant DNA techniques in the generation of antibodies, one needs not be confined to the sequences of amino acids found in natural antibodies; antibodies can be redesigned to obtain desired characteristics. The possible variations are many and range from the changing of just one or a few amino acids to the complete redesign of, for example, the variable domain or constant region. Changes in the constant region will, in general, be made in order to improve, reduce or alter characteristics, such as complement fixation (e.g. complement dependent cytotoxicity, CDC), interaction with Fc receptors, and other effector functions (e.g. antibody dependent cellular cytotoxicity, ADCC), pharmacokinetic properties (e.g. binding to the neonatal Fc receptor; FcRn). Changes in the variable domain will be made in order to improve the antigen binding characteristics. In addition to antibodies, immunoglobulins may exist in a variety of other forms including, for example, single-chain or Fv, Fab, and (Fab')2, as well as diabodies, linear antibodies, multivalent or multispecific hybrid antibodies.

As used herein, the term "antibody portion" refers to a fragment of an intact or a full-length chain or antibody, usually the binding or variable region. Said portions, or fragments, should maintain at least one activity of the intact chain/antibody, i.e. they are "functional portions" or "functional fragments". Should they maintain at least one activity, they preferably maintain the target binding property. Examples of antibody portions (or antibody fragments) include, but are not limited to, "single-chain Fv", "single-chain antibodies," "Fv" or "scFv". These terms refer to antibody fragments that comprise the variable domains from both the heavy and light chains, but lack the constant regions, all within a single polypeptide chain. Generally, a single-chain antibody further comprises a polypeptide linker between the VH and VL domains which enables it to form the desired structure that would allow for antigen binding. In specific embodiments, single-chain antibodies can also be bi-specific and/or humanised.

A "Fab fragment" is comprised of one light chain and the variable and CH1 domains of one heavy chain. The heavy chain of a Fab molecule cannot form a disulfide bond with another heavy chain molecule. A "Fab' fragment" that contains one light chain and one heavy chain and contains more of the constant region, between the CH1 and CH2 domains, such that an interchain disulfide bond can be formed between two heavy chains is called a F(ab')2 molecule. A "F(ab')2" contains two light chains and two heavy chains containing a portion of the constant region between the CH1 and CH2 domains, such that an interchain disulfide bond is formed between two heavy chains. Having defined some important terms, it is now possible to focus the attention on particular embodiments of the instant invention.

Examples of known antibodies which can be produced according to the present invention include, but are not limited to, adalimumab, alemtuzumab, belimumab, bevacizumab, canakinumab, certolizumab, pegol, cetuximab, denosumab, eculizumab, golimumab, infliximab, natalizumab, ofatumumab, omalizumab, pertuzumab, ranibizumab, rituximab, siltuximab, tocilizumab, trastuzumab, ustekinumab or vedolizomab.

The term "subject" is intended to include (but not limited to) mammals such as humans, dogs, cows, horses, sheep, goats, cats, mice, rabbits, or rats. More preferably, the subject is a human. The terms "Inducing agent", "inducer" or "productivity enhancer" refer to a compound allowing an increase of the protein production when added in cell cultures. For instance, one of the inducers known for *E. coli* production is IPTG (Isopropyl β-D-1-thiogalactopyranoside); and inducers for CHO production are among others sodium butyrate, doxycycline or dexamethasone.

The present invention provides methods and compositions for increasing production of a recombinant protein while maintaining viable cell density and avoiding substantial decrease in cell viability over a production period. The present invention is based on the optimisation of cell culture conditions for protein manufacturing, such as production of antibodies or antigen-binding fragments, resulting in increased production of a recombinant protein while maintaining viable cell density and avoiding substantial decrease in cell viability over a production period.

The inventors have surprisingly found that under cell culture conditions containing or supplemented with a triazine dye, the production of a recombinant protein can be increased (i.e. the titre and/or specific productivity is increased), the cell density is increased as well or at least maintained and substantial or significant decrease in cell viability over a production period is avoided. Thus during the cell culture production run, when it is desirable to increase titre of a recombinant protein being produced, the cell culture can be supplemented with a triazine dye, such as Cibacron Blue 3GA, Reactive Red 120, Reactive Yellow 86, Reactive Green 19, Reactive Blue 4, Reactive Brown 10. Alternatively, the cell culture medium can already comprise said triazine dye.

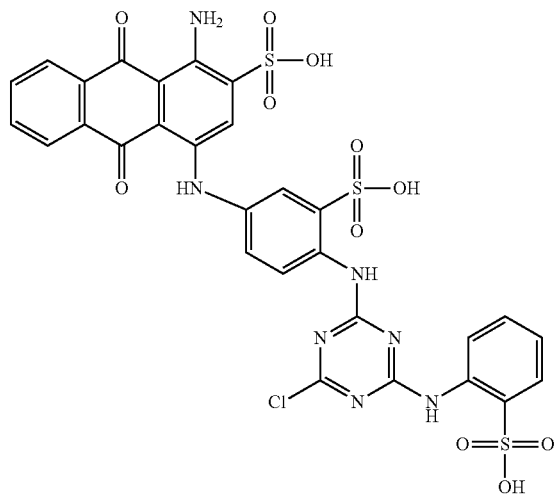

Cibacron Blue 3GA

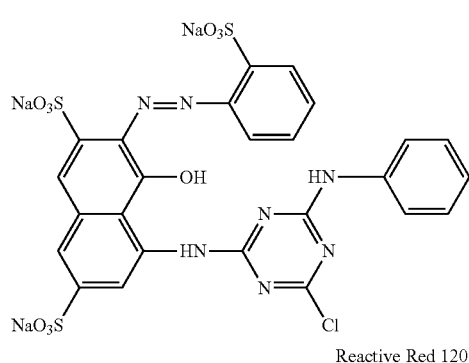
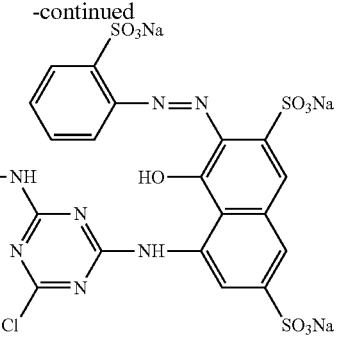

Reactive Red 120

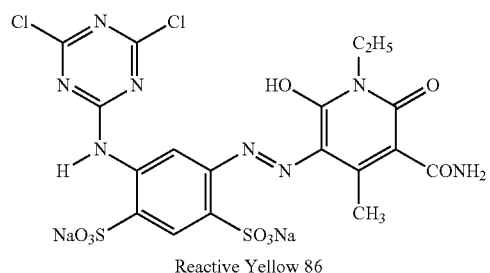

Reactive Yellow 86

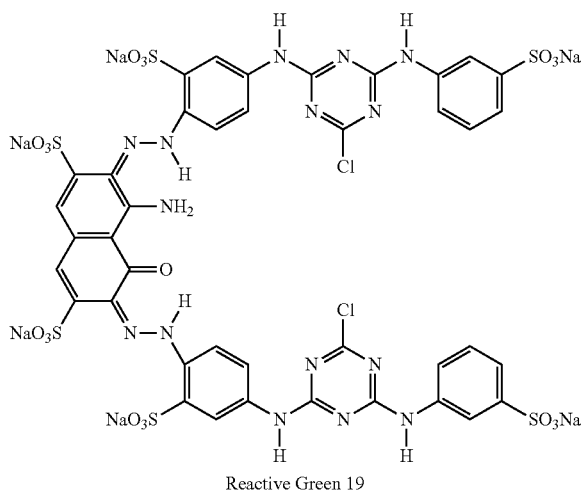

Reactive Green 19

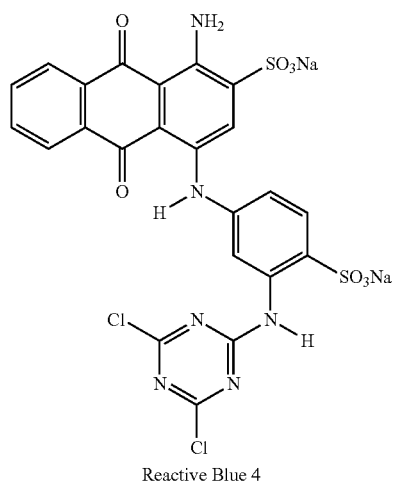

Reactive Blue 4

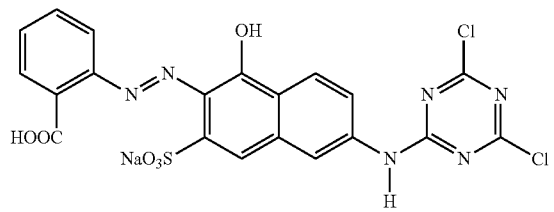

Reactive Brown 10

In one aspect the invention provides a method of increasing production of a recombinant protein, said method comprising culturing a host cell expressing said protein in cell culture medium comprising an effective amount of a triazine dye or supplemented with an effective amount of a triazine dye. The triazine dye is preferably selected from the group comprising Cibacron Blue 3GA, Reactive Red 120, Reactive Yellow 86, Reactive Green 19, Reactive Blue 4, Reactive Brown 10. In some preferred embodiments, the triazine dye is Cibacron Blue 3GA or Reactive Red 120. In further preferred embodiments, the host cell is Chinese Hamster Ovary (CHO) cells. Alternatively, the invention provides a method of increasing production of a recombinant protein, said method comprising culturing a host cell expressing said protein in cell culture medium complemented with at least one feed comprising an effective amount of a triazine dye. The triazine dye is preferably selected from the group comprising Cibacron Blue 3GA, Reactive Red 120, Reactive Yellow 86, Reactive Green 19, Reactive Blue 4, Reactive Brown 10. In some preferred embodiments, the triazine dye is Cibacron Blue 3GA or Reactive Red 120. In further preferred embodiments, the host cell is Chinese Hamster Ovary (CHO) cells.

In a further aspect the invention provides a method of culturing a host cell that expresses a recombinant protein, said method comprising culturing said host cell in cell culture medium comprising an effective amount of a triazine dye or supplemented with an effective amount of a triazine dye. The triazine dye is preferably selected from the group comprising Cibacron Blue 3GA, Reactive Red 120, Reactive Yellow 86, Reactive Green 19, Reactive Blue 4, Reactive Brown 10. In some preferred embodiments, the triazine dye is Cibacron Blue 3GA or Reactive Red 120. In further preferred embodiments, the host cell is Chinese Hamster Ovary (CHO) cells. In another aspect the invention provides a composition comprising a cell culture medium comprising an effective amount of a triazine dye or supplemented with an effective amount of a triazine dye. The triazine dye is preferably selected from the group comprising Cibacron Blue 3GA, Reactive Red 120, Reactive Yellow 86, Reactive Green 19, Reactive Blue 4, Reactive Brown 10. In some preferred embodiments, the triazine dye is Cibacron Blue 3GA or Reactive Red 120.

In a further aspect the invention provides the use of a triazine dye in a cell culture medium for increasing production of recombinant proteins. The triazine dye is preferably selected from the group comprising Cibacron Blue 3GA, Reactive Red 120, Reactive Yellow 86, Reactive Green 19, Reactive Blue 4, Reactive Brown 10. In some preferred embodiments, the triazine dye is Cibacron Blue 3GA or Reactive Red 120.

In the context of the invention as a whole, an effective amount of a triazine dye, such as Cibacron Blue 3GA or Reactive Red 120, is the amount of a triazine dye present in a cell culture medium at the start of the culture or added to a cell culture (or a cell culture medium), as a supplement or as a feed, that will increase expression of the recombinant protein in host cells, and possibly also increase cell density, by a detectable amount when compared to the cells grown without a triazine dye or any other inducer. The triazine dye, such as Cibacron Blue 3GA or Reactive Red 120, is preferably present in a cell culture medium at the start of the culture or added to a cell culture (or cell culture medium), as a supplement or as a feed, at a concentration of or of about 0.01 µM to 150 µM, preferably 0.1 µM to 100 µM, more preferably 1 µM to 90 µM. In some embodiments, the concentration of the triazine dye can be of or of about 0.4 µM, 0.5 µM, 0.9 µM, 1 µM, 5 µM, 8 µM, 10 µM, 15 µM, 20 µM, 25 µM, 30 µM, 35 µM, 40 µM, 45 µM, 50 µM, 60 µM, 70 µM, 80 µM, 85 µM, 90 µM (concentration of triazine dye once in the culture medium in the culture system). For example, but not by way of limitation, by adjusting the concentration of a triazine dye, the production of secreted recombinant protein can be modulated (i.e. increased).

In the context of the invention as a whole, when a triazine dye is present in a cell culture medium at the start of the culture or added to a cell culture (or cell culture medium), as a supplement or as a feed, cell viability does not substantially or significantly decrease and production of the recombinant protein is increased relative to cells grown without a triazine dye or any other inducer.

As used herein, the phrase "cell viability does not substantially or significantly decrease" when compared to cells grown without a triazine dye or any other inducer, means that cell viability does not decrease any more than about 15% compared to the control cultures (i.e. cells grown without a triazine dye or any other inducer).

For the purposes of this invention, the cell culture medium is a medium suitable for growth of animal cells, such as mammalian cells, in in vitro cell culture. Cell culture media formulations are well known in the art. Cell culture media may be supplemented with additional components such as amino acids, salts, sugars, vitamins, hormones, and growth factors, depending on the needs of the cells in culture.

Preferably, the cell culture media are free of animal components; they can be serum-free and/or protein-free.

In certain embodiments of the present invention, the cell culture medium is supplemented with the triazine dye, for example, at the start of culture, and/or in a fed-batch or in a continuous manner. The addition of the triazine dye supplement may be based on measured intermediate titre.

In an embodiment of the present invention, the host cell is preferably a mammalian host cell (herein also refer to as a mammalian cell) including, but not limited to, HeLa, Cos, 3T3, myeloma cell lines (for instance NS0, SP2/0), and Chinese hamster ovary (CHO) cells. In a preferred embodiment, the host cell is Chinese Hamster Ovary (CHO) cells.

In the context of the invention as a whole, the recombinant cell, preferably mammalian cell, is grown in a culture system such as a bioreactor. The bioreactor is inoculated with viable cells in a culture medium. Said culture medium can already comprise the triazine dye or can be supplemented with said triazine dye at the start of the culture and/or at any time after the start of the culture. Preferably the culture medium is serum free and/or protein-free. Once inoculated into the production bioreactor the recombinant cells undergo an exponential growth phase. The growth phase can be maintained using a fed-batch process with bolus feeds of a feed medium optionally supplemented with said triazine dye. Preferably the feed medium is serum-free and/or protein-free. The supplemental bolus feeds typically begin shortly after the cells are inoculated into the bioreactor, at a time when it is anticipated or determined that the cell culture needs feeding. For example, supplemental feeds can begin on or about day 3 or 4 of the culture or a day or two earlier or later. The culture may receive one, two, three, or more bolus feeds during the growth phase. Any one of these bolus feeds can optionally be supplemented with the triazine dye. The supplementation or the feed with the triazine dye can be done at the start of the culture, in fed-batch, and/or in continuous manner. The culture medium can comprise a sugar, such as glucose or be supplemented by a sugar, such as glucose. Said supplementation can be done at the start of the culture, in fed-batch, and/or in continuous manner.

The methods, compositions and uses according to the present invention may be used to improve the production of recombinant proteins in multistep culture processes. In a multiple stage process, cells are cultured in two or more distinct phases. For example cells are cultured first in one or more growth phases, under conditions improving cell proliferation and viability, then transferred to production phase(s), under conditions improving protein production. In a multistep culture process, some conditions may change from one step (or one phase) to the other: media composition, shift of pH, shift of temperature, etc. The growth phase can be performed at a temperature higher than in production phase. For example, the growth phase can be performed at a first temperature from about 35° C. to about 38° C., and then the temperature is shifted for the production phase to a second temperature from about 29° C. to about 37° C. The cell cultures can be maintained in production phase for days or even weeks before harvest.

The cell lines (also referred to as "recombinant cells" or "host cells") used in the invention are genetically engineered to express a protein of commercial or scientific interest. Methods and vectors for genetically engineering of cells and/or cell lines to express a polypeptide of interest are well known to those of skill in the art; for example, various techniques are illustrated in Ausubel et al. (1988, and updates) or Sambrook et al. (1989, and updates). The methods of the invention can be used to culture cells that express recombinant proteins of interest. The recombinant proteins are usually secreted into the culture medium from which they can be recovered. The recovered proteins can then be purified, or partially purified using known processes and products available from commercial vendors. The purified proteins can then be formulated as pharmaceutical compositions. Suitable formulations for pharmaceutical compositions include those described in Remington's Pharmaceutical Sciences, 1995.

In the context of the invention as a whole, the recombinant protein is selected from the group consisting of an antibody or antigen binding fragment thereof, such as a human antibody or antigen-binding portion thereof, a humanised antibody or antigen-binding portion thereof, a chimeric antibody or antigen-binding portion thereof, a recombinant fusion protein, a growth factor, a hormone, or a cytokine.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

The foregoing description will be more fully understood with reference to the following examples. Such Examples, are, however, exemplary of methods of practising the present invention and are not intended to limit the scope of the invention.

EXAMPLES

Material and Methods
I. Cells, Cell Expansion and Cell Growth
1) Cells
  Assays were performed with 2 CHO cell lines:
  CHO-S cells expressing IgG1 mAb1, herein "Cells mAb1" or "mAb1 cells". "mAb1" is a fully human monoclonal antibody directed against a soluble protein. Its isoelectric point (pI) is about 8.20-8.30.
  CHO-K1 cells expressing IgG1 mAb2, herein "Cells mAb2" or "mAb2 cells". "mAb2" is a humanised monoclonal antibody directed against a receptor found on the cell membrane. Its isoelectric point (pI) is about 9.30.
2) Cell Expansion
  Cell expansion was performed in tubes in a medium suitable for cell expansion. Assays in fed-batch started after at least one week expansion.
3) Inoculation
  Cells expressing mAb2 were inoculated at $0.2 \times 10^6$ cells per millilitre (mL), whereas cells expressing mAb1 were inoculated at $0.3 \times 10^6$ cells per mL.
4) Fed-Batch
  All assays were performed in fed-batch culture. The host cells were cultured in fed-batch system either in microplates ("Deep well plate") or in Spin Tubes®, and incubated at 36.5° C., 90% relative humidity, 5% $CO_2$ and 320 rpm shaking during 14 days.

II. Analytical Methods
  Viable cell density and viability were measured with the Guava easyCyte® flow cytometer or with the ViCell.
  Antibody titres were measured with the fortêBIO Octet® or with Biacore C®.
  Glycosylation profiles were established by capillary gel electrophoresis with laser-induced fluorescence (CGE-LIF). Dosages of aggregates and fragments were performed respectively via Size Exclusion High Performance Liquid Chromatography (SE-HPLC) and SDS-capillary gel electrophoresis.
Results and Discussions Example 1—Reactive Red 120

The activity of Reactive Red 120 was tested in microplates on host cells expressing antibody mAb1 and in Spin tubes on host cells expressing antibodies mAb1 or mAb2.

The host cells expressing mAb1 were first cultured in presence of about 0.4 µM to about 17 µM of Reactive Red 120 in microplates. The cell density, the cell viability and the titre were measured during the culture (FIGS. 1A-1C). At these concentrations, Reactive Red 120 increased significantly the viable cell density and the titre, while the cell viability was (slightly) reduced. Specifically, at 17.3 µM, the viable cell density increased by factor 1.5 on day 7 and the titre increased by factor 1.3 on day 14. The viability was similar to the one of the control until day 10, and slightly decreased compared to the control at the end of the production process.

Figure 1:
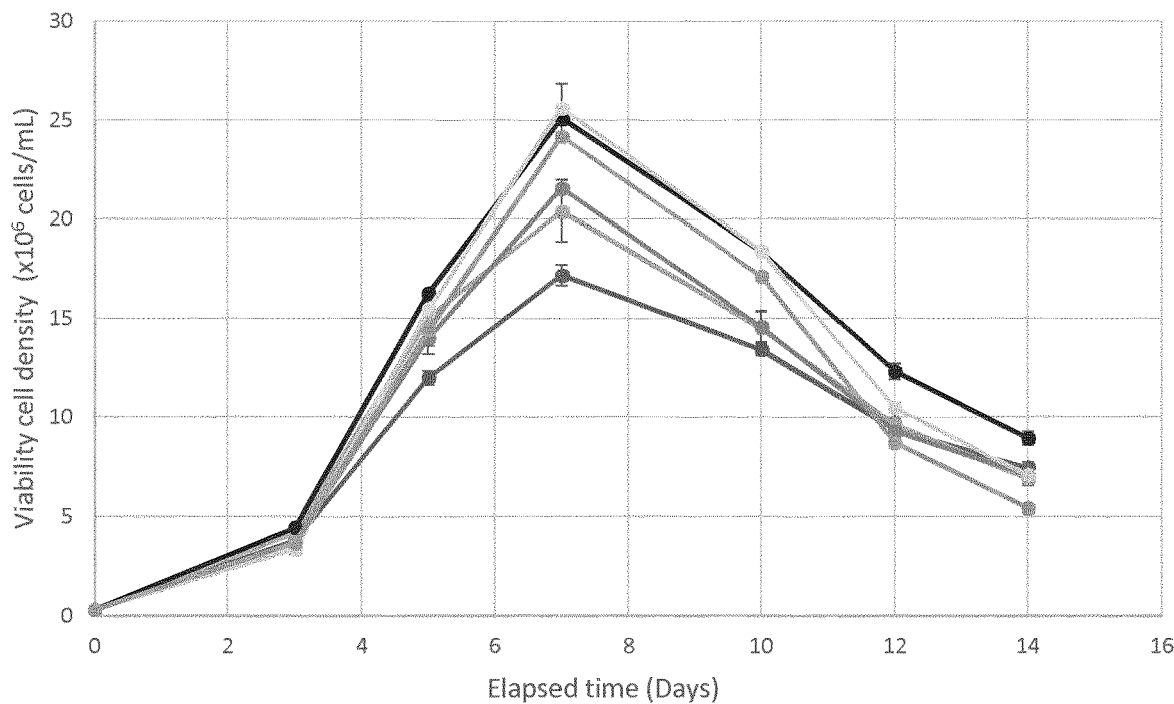
FIG. 1 shows the density of viable cells (Guava®, FIG. 1A) and viability (Guava®, FIG. 1B) related to time (until day 14), as well as the titre at day 14 (Octet®, FIG. 1C) for the host cells expressing antibodies mAb1 cultured with different concentrations of Reactive Red 120 in microplates. The results are shown as average value±standard deviation. Same legend for FIGS. 1A and 1B.
Figure 1:
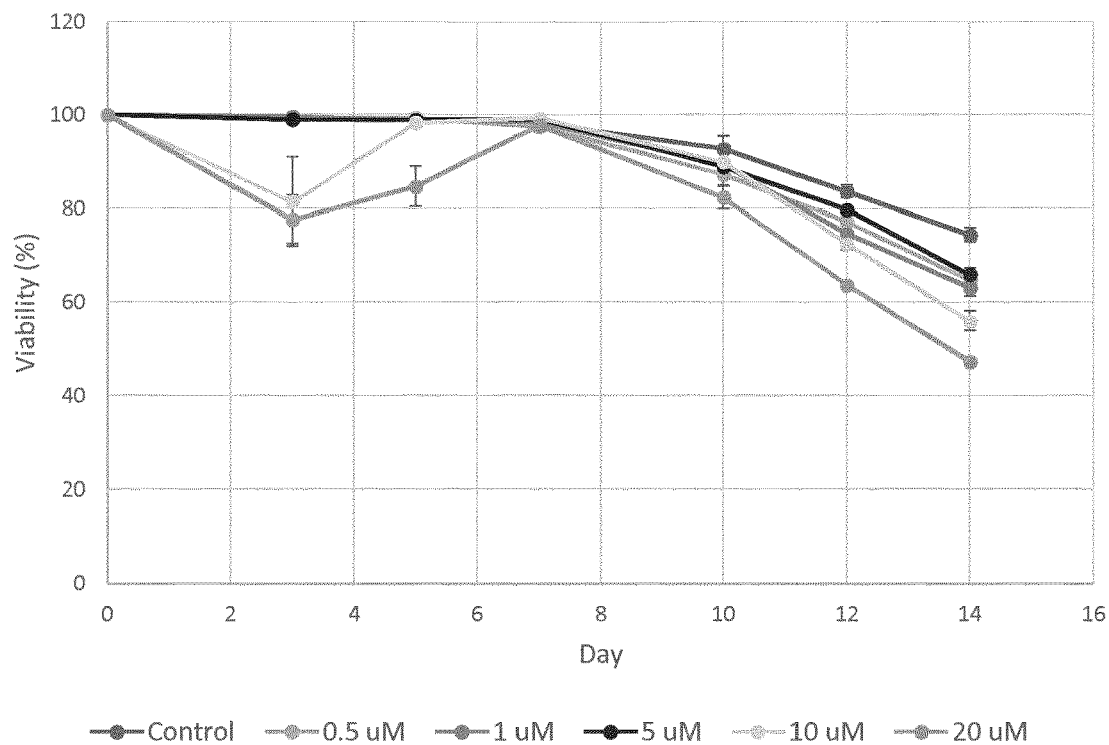
Figure 2:
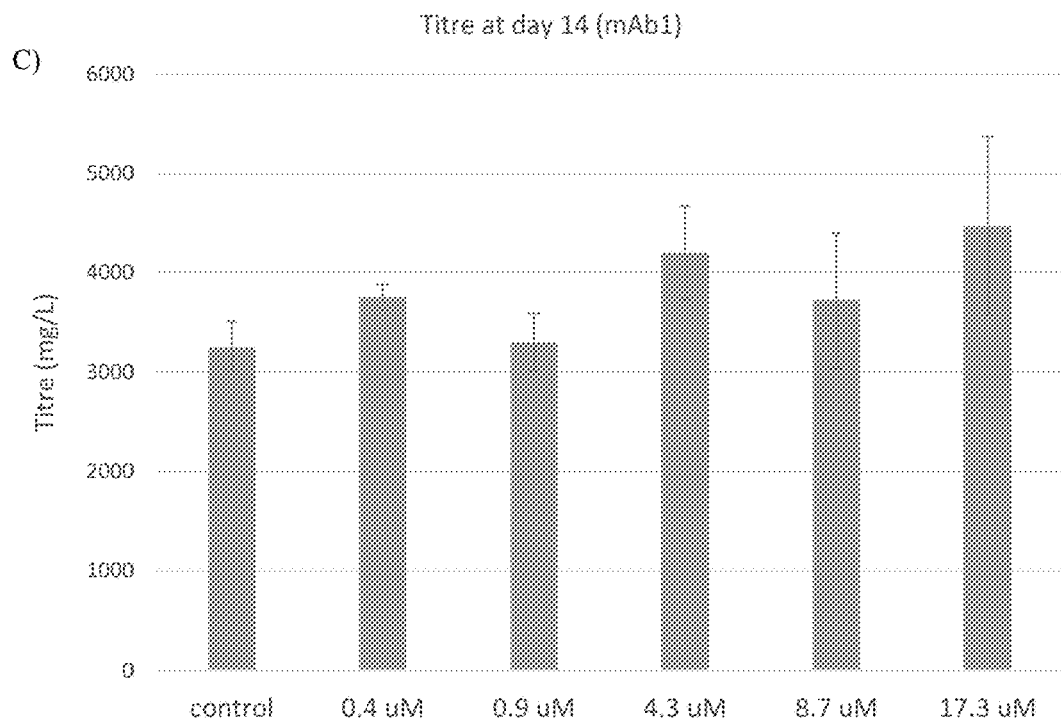
FIG. 2 shows quality analysis of the secreted antibody mAb1 at different concentrations of Reactive Red 120 in microplate. Glycosylation profiles are analysed by CGE-LIF assay. Gal=Galactosylation; Man=Mannosylation; Fuc=Fucosylation; Sial=sialylation; Ukn=unknown.
Figure 2:
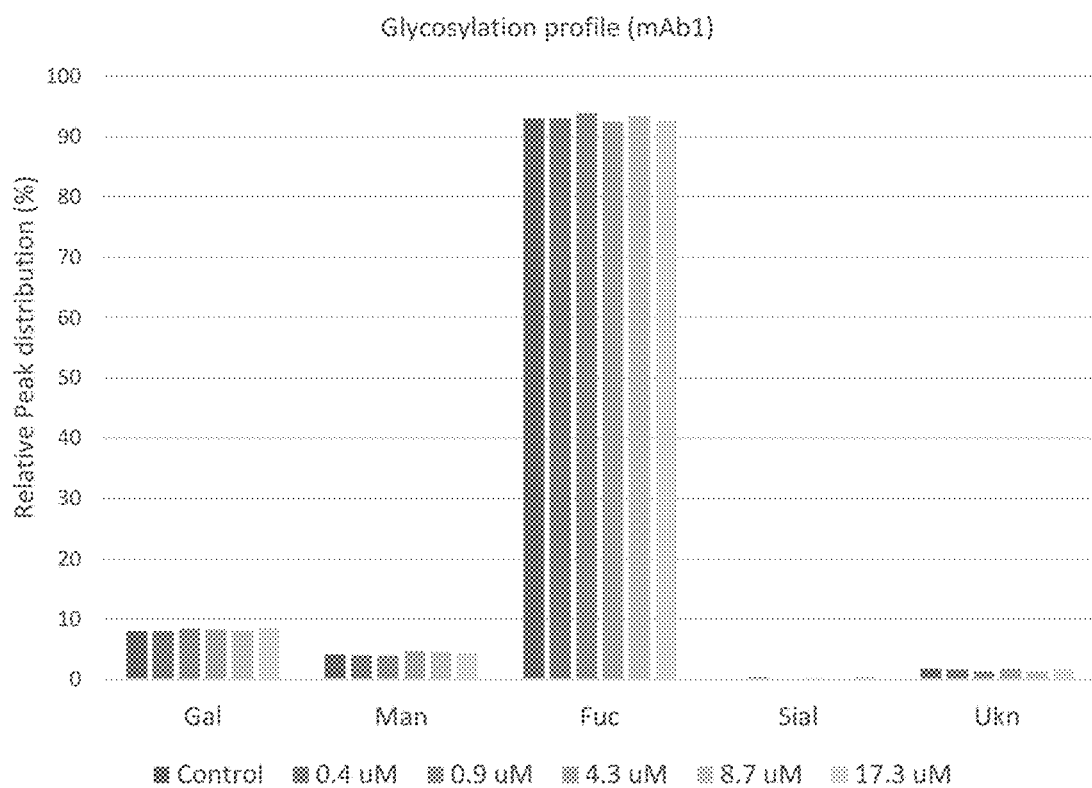
Figure 3:
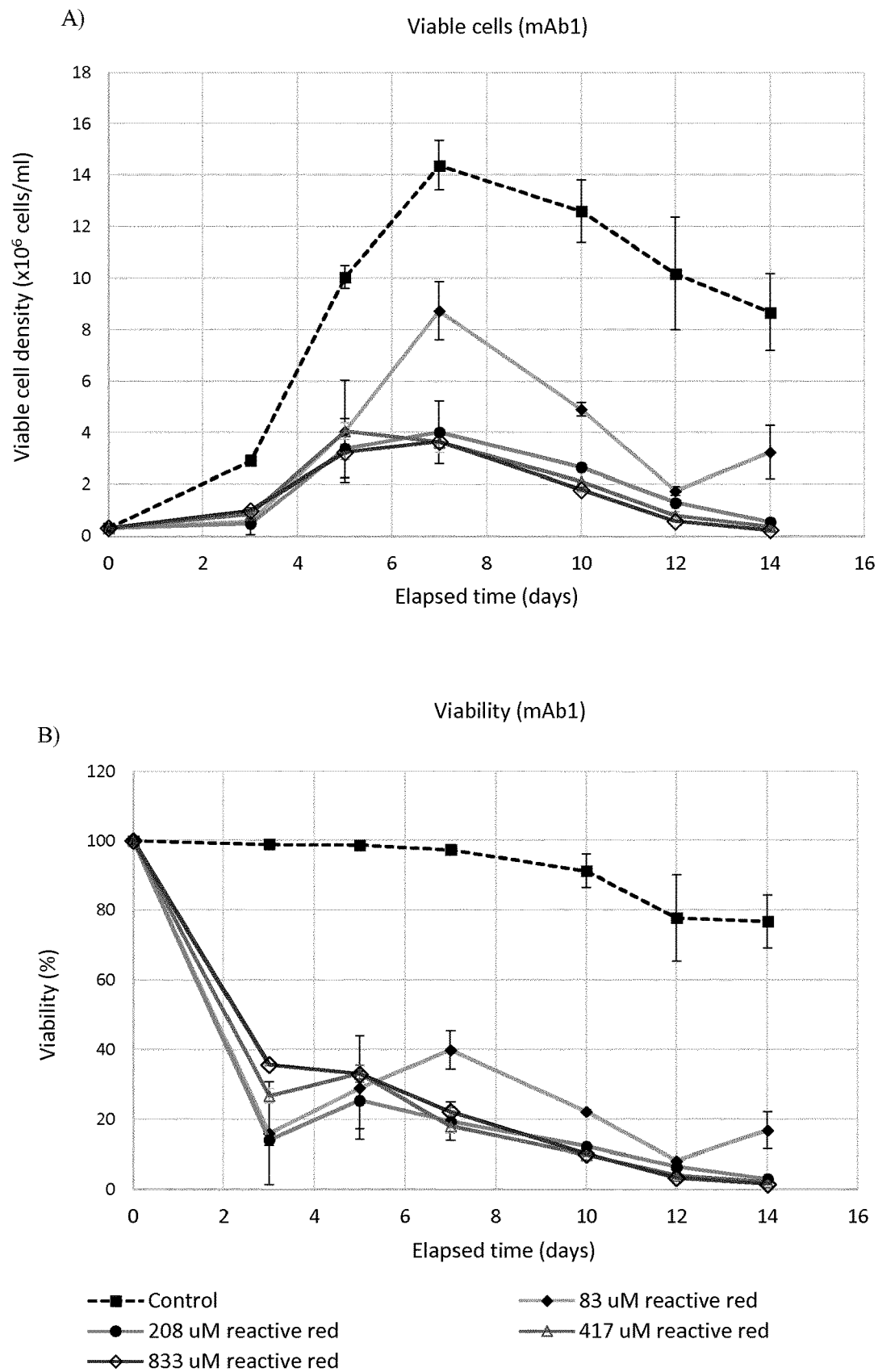
FIG. 3 shows the viable cell density (Guava, FIG. 3A) and viability (Guava®, FIG. 3B) related to time (until day 14), as well as the titre at day 14 (Octet®, FIG. 1C) for the host cells expressing the antibody mAb1 cultured at different concentrations of Reactive Red 120 in microplates. The results are presented as average value±standard deviation. Same legend for FIGS. 3A and 3B.
Figure 4:
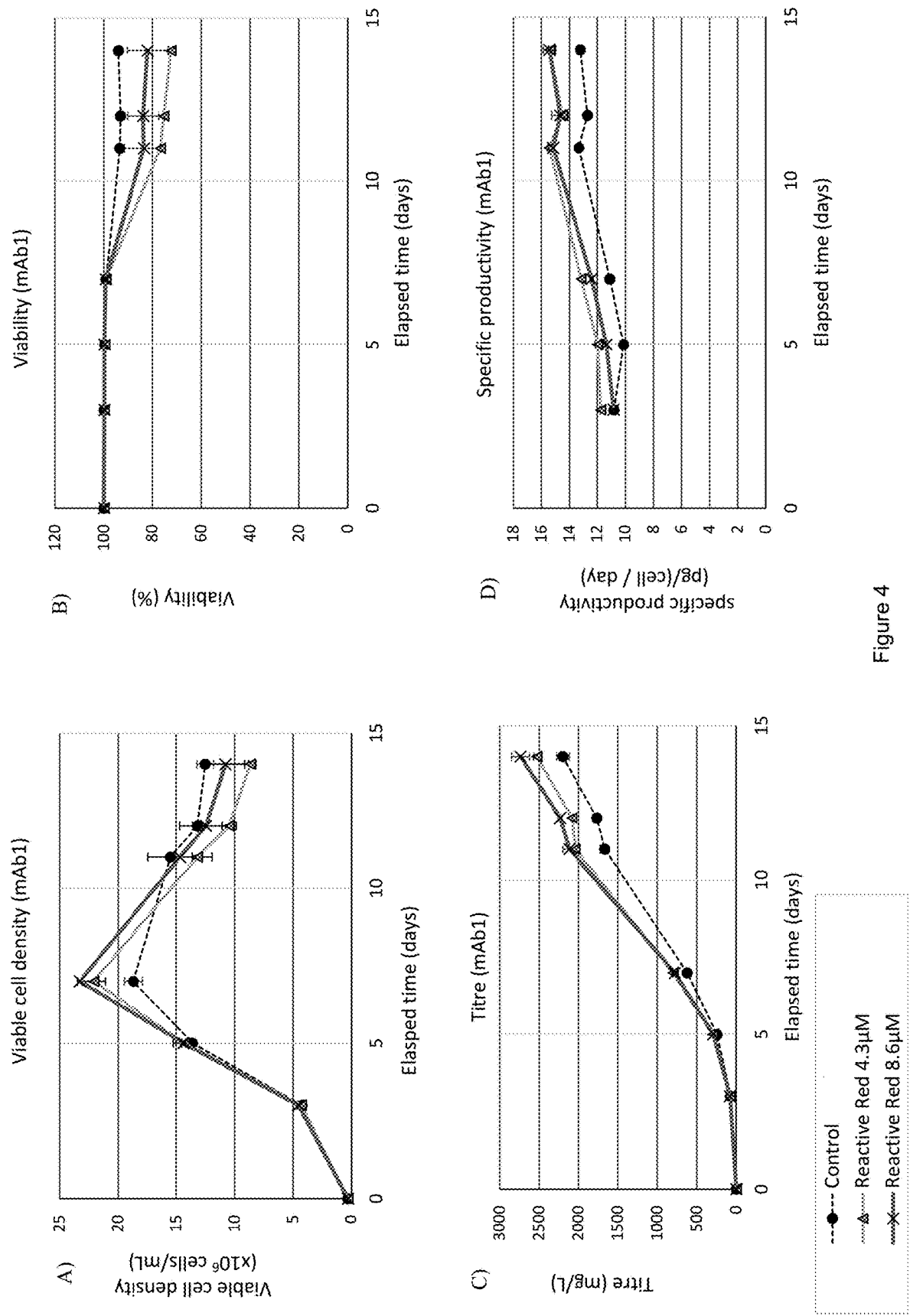
FIG. 4 shows the viable cell density (ViCell®, FIGS. 4A and 4E), the viability (ViCell®, FIGS. 4B and 4F), the titre (Biacore®, FIGS. 4C and 4G), the specific productivity (FIGS. 4D and 4H) in relation to time (until day 14) for the host cells expressing the antibody mAb1 (left) and the antibody mAb2 (right) cultured with different concentrations of Reactive Red 120 in Spin Tubes (average value±standard deviation). One legend for FIGS. 4A to 4D and one for FIGS. 4E to 4H.
Figure 5:
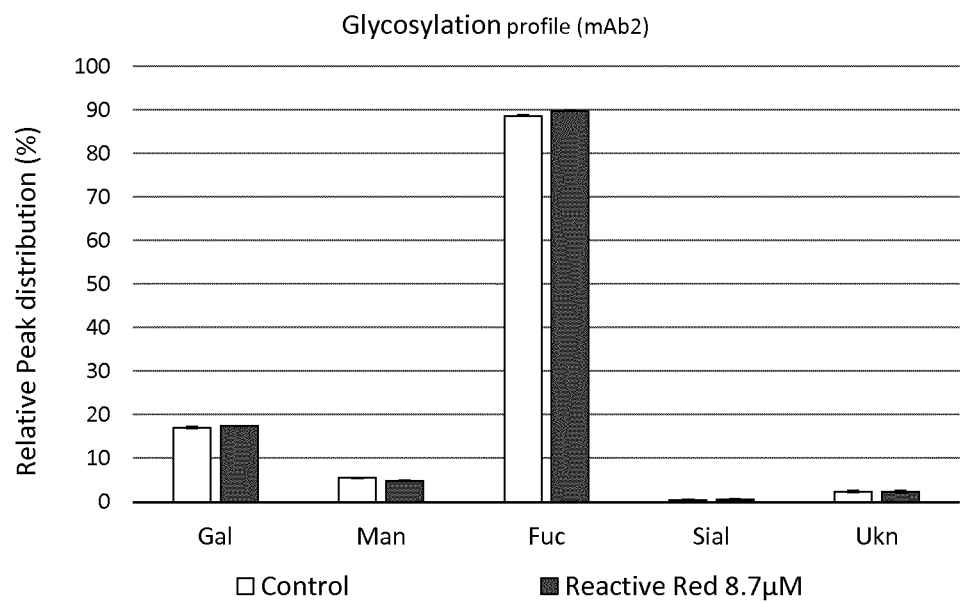
FIG. 5 shows glycosylation profile (CGE-LIF, FIG. 5A) as well as aggregates and fragments ratios (SE HPLC and SDS-capillary gel electrophoresis, FIG. 5B) for the antibody mAb2 when the host cells are cultured at different concentrations of Reactive Red 120 in Spin tubes. The results are presented as average values±standard deviation.
Figure 5:
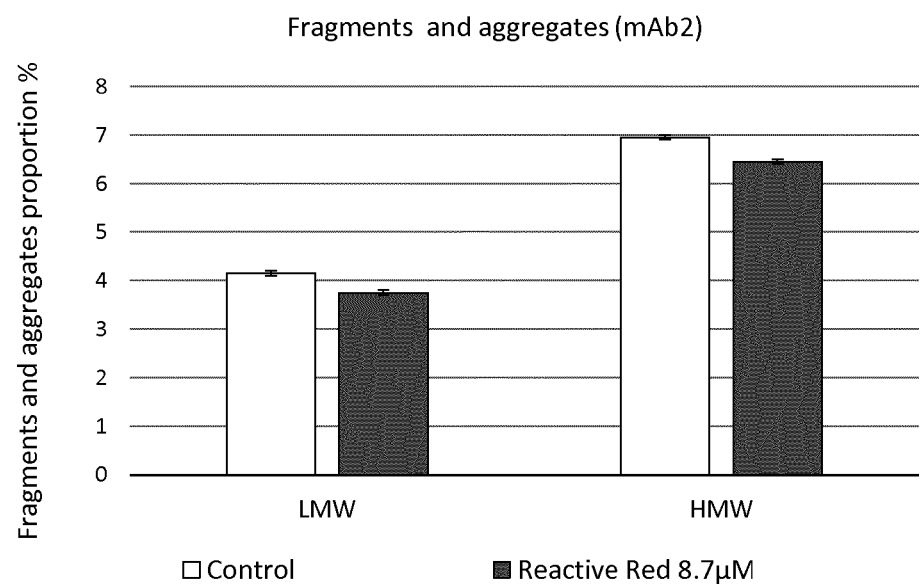

It is also interesting to mention that Reactive Red 120 does not have any influence on glycosylation of antibody mAb1 at tested concentrations (FIG. 2). This is very useful aspect as for example Reactive Red 120 can be added to the culture medium at the end of the culture process in order to increase cell growth and titre, without modifying the quality of the secreted recombinant protein.

At concentration of about 17 µM, the cell density and the titre were at maximum and the toxicity limit of Reactive Red 120 did not seem to have been reached. This suggests that increased concentrations of Reactive Red 120 can be used to obtain even better results.

According to further assays in microplates on host cells expressing antibody mAb1 with Reactive Red 120 at concentrations ranging from about 83 µM to about 833 µM, it was found that both the viable cell density and the cell viability decrease significantly, while the titre remained superior or equal to what was obtained with control cells (FIG. 3A-3C). With these concentrations, the maximum titre was obtained with Reactive Red 120 concentration at 83 µM, which is 1.2 fold greater than what was obtained with control cells. Above 83 µM concentration, Reactive Red 120 becomes toxic, the titre decreased and the quality of the recombinant protein was affected. This suggests that the concentration of Reactive Red 120 should not exceed about 83 µM.

In order to confirm the results obtained with host cells expressing antibody mAb1 in microplates and evaluate the reproducibility of these results with other host cells expressing a different antibody (mAb2), Reactive Red 120 was added in culture medium in Spin Tubes at concentrations of about 4.3 and/or about 8.5 µM. The results of the assays obtained on culture or on the compound are presented in FIG. 4 (FIGS. 4A-4D for mAb1 and 4E-4H for mAb2). The data confirmed the previous results obtained with the host cells expressing antibody mAb1 in microplates. Namely the viable cell density increased (see for instance days 5-9) and the cell viability is only slightly affected after day 10 compared to the control. Also the titre increased by factor 1.2 at 8.6 µM concentration of Reactive Red 120. Similar results are observed for mAb2: Reactive Red 120 allowed the increase of the titre and the specific productivity of the host cells expressing the antibodies mAb2. The viability was maintained, compared to the control, until the end of the culture. The glycosylation profile of the antibodies mAb1 and mAb2 did not vary (see FIG. 5A, data shown for mAb2 only). Interestingly, the percentage of fragments and aggregates was slightly decreased (see also FIG. 5B, data shown for mAb2 only).

Example 2—Cibacron Blue 3GA

As Reactive Red 120, Cibacron Blue 3GA had an interesting impact on the titre. In addition to assays in microplates on the host cells expressing mAb1, the efficacy of Cibacron Blue 3GA was evaluated on the host cells expressing antibodies mAb1 or mAb2 in Spin Tubes.

The host cells expressing antibody mAb1 were cultured in microplates with different concentrations of Cibacron Blue 3GA (0.4 µM-416.7 µM) in the culture medium. The cell density, the cell viability and the titre are presented in FIGS. 6A-6C. Up to concentrations ranging from 25 µM and 41.7 µM, the viable cell density and the titre increased significantly. Specifically, the quantity of secreted recombinant protein reached 1.5 fold comparing to the control at concentration about 8.3 to about 41.7 µM. At a concentration of about 83 µM, the titre was still significantly increased. However, if Cibacron Blue 3GA was added in the culture medium in much higher concentrations, such as about 167 µM or about 417 µM, the cell viability decreased and impact on the titre was observed. The quality of the secreted recombinant protein was not affected (no deep impact on the glycosylation profile). Thus Cibacron Blue 3GA could increase the titre by factor 1.5 without significantly modifying the glycosylation profile of the secreted recombinant protein (see FIG. 7).

The efficacy of Cibacron Blue 3GA was also evaluated on the host cells expressing antibodies mAb1 or mAb2 in Spin tubes. The chosen concentration of Cibacron Blue 3GA was 8.5 µM, because it allowed an important increase of titre of antibody mAb1 in microplates. The obtained results are presented on FIG. 8 (FIGS. 8A-8D for mAb1 and 8E-8H for mAb2). For the host cells expressing antibody mAb1, the maximum density of viable cells increased at days 6-9. The specific productivity was also significantly increased. The combination of these two factors allowed to increase the titre at the end of the culture by factor 1.25. On the other hand, the observed results revealed a decrease of viability starting on day 7, compared to the control. This decrease is still acceptable. Cibacron Blue 3GA was also tested at similar concentrations on the host cells expressing antibodies mAb2. As observed for the host cells expressing mAb1, the productivity of antibodies mAb2 increased and the titre was multiplied by 1.2 at the end of cell culture. The quality of tested antibodies mAb1 and mAb2 is not affected in presence of Cibacron Blue 3GA (see FIGS. 9A and 9C). Interestingly, the percentage of fragments and aggregates was slightly decreased (see FIGS. 9B and 9D).

Overall Conclusion:

Triazine dyes such as Reactive red 120 and Cibacron Blue 3GA are therefore very promising compounds for increasing the quantity of the produced recombinant protein, without modifying the glycosylation profile of the protein or having a negative impact on cell viability. Triazine dyes could thus be used as inducers, without the drawback on cell viability observed with sodium butyrate in the literature.

The skilled person will understand from the results of examples 1 and 2 that he can use a triazine dye for modulating the production profile of any antibodies and any proteins, whatever the cell line that is used for production. The optimal concentration of triazine dye to be added in the cell culture media will have to be determined case by case. This determination can be done without involving any inventive skill, based on the teaching of the present invention. The skilled person will also understand that he can use a triazine dye in any method for producing a protein such as an antibody, even if he does not aim to reach a particular production profile, but simply to increase cell productivity and to obtain more efficient production runs, while maintaining acceptable cell viability over a longer time.

REFERENCES

1) Cell Culture Technology for Pharmaceutical and Cell-Based Therapies, Sadettin Ozturk, Wei-Shou Hu, ed., CRC Press (2005)
2) Kim et al., 2004, Biotechnol. Prog., 20:1788-1796
3) Voisard et al., 2003, Biotechnol. Bioeng. 82:751-765
4) Ausubel et al., 1988 and updates, Current Protocols in Molecular Biology, eds. Wiley & Sons, New York.
5) Sambrook et al., 1989 and updates, Molecular Cloning: A Laboratory Manual, Cold Spring Laboratory Press.

The invention claimed is:

1. A method of increasing production of a recombinant protein, said method comprising culturing a mammalian host cell expressing said protein in a cell culture medium comprising a triazine dye, wherein the triazine dye is selected from the group consisting of Cibacron Blue 3GA and Reactive Red 120 and wherein the triazine dye is present at a concentration of 0.01 µM to 150 µM, wherein production of the recombinant protein is thereby increased.

2. The method of claim 1, wherein the host cell is Chinese Hamster Ovary (CHO) cells.

3. The method of claim 1, wherein the recombinant protein is selected from the group consisting of an antibody or antigen binding fragment thereof, a human antibody or antigen-binding portion thereof, a humanized antibody or antigen-binding portion thereof, a chimeric antibody or antigen-binding portion thereof, a recombinant fusion protein, a growth factor, a hormone, and a cytokine.

* * * * *